United States Patent [19]

Ansmann et al.

[11] Patent Number: 5,795,978
[45] Date of Patent: Aug. 18, 1998

[54] EMULSIFIERS

[75] Inventors: Achim Ansmann, Erkrath; Rolf Kawa, Monheim; Michael Nitsche, Solingen; Helga Gondek, Duesseldorf, all of Germany

[73] Assignee: Henkel Kommanditgesellschaft auf Aktien, Duesseldorf, Germany

[21] Appl. No.: 748,882

[22] Filed: Nov. 14, 1996

Related U.S. Application Data

[60] Provisional application No. 60/014,139, Mar. 25, 1996.

[30] Foreign Application Priority Data

Nov. 15, 1995 [DE] Germany ............... 195 42 572.3
Sep. 5, 1996 [DE] Germany ............... 196 36 039.0

[51] Int. Cl.$^6$ .............. C07H 15/04; C07H 1/00; C11D 3/22; A61K 9/10
[52] U.S. Cl. .............. 536/120; 536/123.1; 514/937; 514/938; 514/943; 510/417; 510/470
[58] Field of Search .............. 536/4.1, 120, 123.1; 510/417, 470; 514/937, 938, 943

[56] References Cited

U.S. PATENT DOCUMENTS

| | | | |
|---|---|---|---|
| 4,172,887 | 10/1979 | Vanlerberghe et al. | 424/70 |
| 4,657,999 | 4/1987 | Hoefer et al. | 526/200 |
| 5,374,716 | 12/1994 | Biermann et al. | 536/18.6 |
| 5,431,840 | 7/1995 | Soldanski et al. | 510/241 |
| 5,476,610 | 12/1995 | Schmid et al. | 510/532 |
| 5,489,395 | 2/1996 | Behler et al. | 510/427 |
| 5,494,938 | 2/1996 | Kawa et al. | 514/786 |
| 5,599,787 | 2/1997 | Schmid et al. | 510/535 |
| 5,656,200 | 8/1997 | Boettcher et al. | 252/307 |

FOREIGN PATENT DOCUMENTS

| | | |
|---|---|---|
| 301 298 | 3/1993 | European Pat. Off. . |
| 553 241 | 4/1995 | European Pat. Off. . |
| 2 252 840 | 8/1975 | France . |
| 1 165 574 | 3/1964 | Germany . |
| 20 24 051 | 7/1986 | Germany . |
| WO 90/03977 | 4/1990 | WIPO . |
| WO 92/07543 | 5/1992 | WIPO . |
| 95/06702 | 3/1995 | WIPO . |
| 95/31525 | 11/1995 | WIPO . |

OTHER PUBLICATIONS

J. Falbe, "Katalysatoren, Tenside und Mineralöladditive (Catalysts, Surfactants and Mineral Oil Additives)", Thieme Verlag, Stuttgart, 1978, pp. 123–217.

"Kosmetische Färbemittel" of the Farbstoffkommission der Deutschen Forschungsgemeinschaft, Verlag Chemie, Weinheim, 1984, pp. 81–106.

*Primary Examiner*—John Kight
*Assistant Examiner*—Howard C. Lee
*Attorney, Agent, or Firm*—Wayne C. Jaeschke; John E. Drach; Steven J. Trzaska

[57] ABSTRACT

Emulsifiers particularly suitable for the production of storable, high-viscosity and sensorially light o/w emulsions contain from about 43% to about 99% by weight of an alkyl and/or alkenyl oligoglycoside and from about 1% to about 57% by weight of a fatty alcohol.

12 Claims, No Drawings

EMULSIFIERS

BENEFIT OF EARLIER FILING DATE UNDER 37 CFR 1.78(A)(4)

This application claims the benefit of earlier filed and copending provisional application Ser. No. 60/014,139 filed on Mar. 25, 1996.

BACKGROUND OF THE INVENTION

1. Field of the Invention

This invention relates to new emulsifiers with defined contents of alkyl glycosides and alcohols, to processes for their production and to the use of the emulsifiers for the production of cosmetic and/or pharmaceutical formulations.

2. Description of the Related Art

The use of mixtures of 10 to 40% by weight of alkyl oligoglucosides, 60 to 90% by weight of fatty alcohols and optionally polyglucose for the production of emulsions is known from EP-B1 0 553 241 (SEPPIC). According to the teaching of International patent application WO 92/07543 (Henkel), alkyl oligoglucosides may be used together with fatty alcohols and partial glycerides as cosmetic emulsifiers.

However, it has been found that the known glucoside/fatty alcohol emulsifiers have to be used in relatively large quantities for the production of high-viscosity o/w creams. However, high wax concentrations, i.e. large quantities of the emulsifier mixture, represent an unwanted burden on the skin, particularly in cases where sensorially light products are required.

Accordingly, the problem addressed by the present invention was to provide emulsifiers, preferably for the production of high-viscosity o/w emulsions, which would enable more stable, but at the same time sensorially lighter products to be produced with a reduced quantity of waxes by comparison with the known products.

DESCRIPTION OF THE INVENTION

The present invention relates to emulsifiers containing a) 43 to 99 and preferably 43 to 90% and more preferably 45 to 55% by weight of alkyl and/or alkenyl oligoglycosides and b) 1 to 57 and preferably 10 to 57% and more preferably 45 to 55% by weight of fatty alcohols, with the proviso that the components add up to 100% by weight.

It has surprisingly been found that not only do mixtures of alkyl glycosides and fatty alcohols, which contain the two components in exactly the opposite ratio by weight to known products, have equally high emulsifying power, o/w emulsions of significantly higher viscosity can also be produced with comparable quantities of emulsifier. Conversely, o/w emulsions of comparable viscosity can be produced with smaller quantities of the new emulsifiers so that the required sensorially lighter products can be obtained through the reduced quantity of waxes. The invention includes the observation that particularly viscous and sensorially advantageous emulsions showing high stability in storage can be obtained using hydrophilic waxes, preferably fatty acid partial glycerides.

Alkyl and/or Alkenyl Oligoglycosides

Alkyl and alkenyl oligoglycosides are known nonionic surfactants corresponding to formula (I):

(I)

in which $R^1$ is an optionally hydroxysubstituted, linear or branched alkyl and/or alkenyl radical containing 4 to 54 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, isotridecyl alcohol, myristyl alcohol, cetyl alcohol, isocetyl alcohol, palmitoleyl alcohol, stearyl alcohol, isostearyl alcohol, ricinolyl alcohol, hydroxystearyl alcohol, dihydroxystearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Guerbet alcohols containing 12 to 36 carbon atoms and technical dimerdiol and trimertriol mixtures containing 18 to 36 or 18 to 54 carbon atoms may also be used. Alkyl oligoglucosides based on cetostearyl alcohol, isostearyl alcohol and/or Guerbet alcohols, preferably containing 12 to 18 carbon atoms, with a DP of 1 to 3 are preferred.

Fatty Alcohols

Fatty alcohols in the context of the invention are understood to be primary aliphatic alcohols corresponding to formula (II):

$$R^2OH \qquad (II)$$

in which $R^2$ is an aliphatic, linear or branched, optionally hydroxy-substituted hydrocarbon radical containing 6 to 54 carbon atoms and 0 and/or 1, 2 or 3 double bonds. Typical examples are caproic alcohol, caprylic alcohol, 2-ethylhexyl alcohol, capric alcohol, lauryl alcohol, isotridecyl alcohol, myristyl alcohol, cetyl alcohol, isocetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, ricinolyl alcohol, hydroxystearyl alcohol, dihydroxystearyl alcohol, arachyl alcohol, gadoleyl alcohol, behenyl alcohol, erucyl alcohol and brassidyl alcohol and the technical mixtures thereof which are obtained, for example, in the high-pressure hydrogenation of technical methyl esters based on fats and oils or aldehydes from Roelen's oxosynthesis and which accumulate as monomer fraction in the dimerization of unsaturated fatty alcohols. Other examples are the Guerbet alcohols based on fatty alcohols containing 6 to 18 carbon atoms and technical dimerdiols and trimertriols containing 18 to 36 or 18 to 54 carbon atoms which emanate from the oligomerization and subsequent hydrogenation of unsaturated fatty acids.

Technical fatty alcohols containing 16 to 18 carbon atoms, for example cetostearyl alcohol, isostearyl alcohol and Guerbet alcohols of corresponding chain length are preferred. According to the invention, it is of particular advantage to use mixtures of alkyl oligoglucosides and fatty alcohols which contain identical alkyl radicals, i.e. for example mixtures of cetearyl oligoglucosides and cetearyl alcohol, isostearyl oligoglucosides and isostearyl alcohol or Guerbet alkyl oligoglucosides and the corresponding Guerbet alcohols.

Production Processes

To produce the emulsifiers according to the invention, commercial aqueous glucoside pastes, for example, may be mixed with fatty alcohols in the required ratio and, if desired, the resulting mixture may be completely or partly freed from water.

However, the emulsifiers according to the invention are preferably produced from the technical glucoside/fatty alcohol mixtures which are formed in the production of alkyl oligoglucosides by acid-catalyzed acetalization of glucose with fatty alcohol in excess. These mixtures normally contain around 60 to 80% by weight of fatty alcohol and 20 to 40% by weight of glucosides. Basically, the relatively high glucoside content can be established by two methods: either the fatty alcohol component is depleted to the required extent by a subsequent distillation-based treatment in a thin-layer or falling-film evaporator or the glucoside component is increased by—preferably—water-free glucosides which in turn can be prepared from aqueous pastes by drying with superheated steam or by the removal of water in a flash dryer. Both variants are further subjects of the present invention.

In one preferred embodiment of the invention, glucose and cetyl alcohol are acetalized in known manner, excess fatty alcohol is completely or predominantly removed and stearyl alcohol and/or isostearyl alcohol is/are added in the required amount. If necessary, any polyglucose formed may be removed by means of membranes.

Another preferred process for the production of the emulsifiers according to the invention is characterized in that glucose or starch sirup is first reacted with a short-chain alcohol, for example butanol or a head-fractionated fatty alcohol containing 6 to 10 carbon atoms, to form a lower alkyl glucoside which is then transacetalized with the required long-chain fatty alcohol, preferably cetearyl alcohol. The product of this reaction may then be further worked up as described above.

Commercial Applications

The emulsifiers according to the invention enable stable o/w emulsions to be produced. In contrast to known emulsifiers, which have a higher fatty alcohol content and a lower glucoside content, highly viscous creams, for example, may even be produced with low wax concentrations which results in a significant improvement in the sensorial properties of the product. Accordingly, the present invention also relates to the use of the new emulsifiers for the production of cosmetic and/or pharmaceutical formulations.

Hydrophilic Waxes

In one preferred embodiment of the invention, the new emulsifier mixtures are used together with consistency-imparting hydrophilic waxes. These hydrophilic waxes are solid at room temperature and contain free hydroxyl groups. Typical examples are fatty acid partial glycerides, i.e. technical monoesters and/or diesters of glycerol with fatty acids containing 12 to 18 carbon atoms, such as for example, glycerol mono/dilaurate, palmitate or stearate. Fatty alcohols, for example technical fatty alcohols containing 12 to 22 carbon atoms, namely cetyl alcohol, stearyl alcohol or cetearyl alcohol, may also be used. The hydrophilic waxes are preferably used in quantities of 10 to 30% by weight and preferably in quantities of 2.5 to 10% by weight, based on the emulsifiers.

Advantageous mixtures of the emulsifier components (a) and (b) and hydrophilic waxes (c), which represent another subject of the present invention, have the following compositions for example:

(a) 25 to 45% by weight of alkyl and/or alkenyl oligoglycosides, (b) 25 to 45% by weight of fatty alcohols and (c) 10 to 50% by weight of hydrophilic waxes, for example fatty acid partial glycerides, again with the proviso that the quantities add up to 100% by weight.

Oils

The emulsifiers according to the invention are suitable for the production of emulsions of the o/w type. Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons; also silicone oils, dimethicones or cyclomethicones. The oil may make up 5 to 99% by weight and preferably 10 to 75% by weight of the non-aqueous component of the emulsions.

Surfactants

The emulsions obtainable with the emulsifiers according to the invention may contain anionic, nonionic, cationic and/or amphoteric or zwitterionic surfactants as constituents.

Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217.

Other Auxiliaries and Additives

The emulsions may be used as skin-care formulations, for example day creams, night creams, care creams, nourishing creams, body lotions, emollients and the like and may contain co-emulsifiers, cationic polymers, silicones, superfatting agents, fats, waxes, stabilizers, biogenic agents, glycerol, preservatives, dyes and fragrances as further auxiliaries and additives.

Suitable co-emulsifiers are nonionic, ampholytic and/or zwitterionic interfacially active compounds which are distinguished by a lipophilic, preferably linear, alkyl or alkenyl group and at least one hydrophilic group. This hydrophilic group may be both an ionic group and a nonionic group.

Nonionic emulsifiers contain a polyol group, a polyalkylene glycol ether group or a combination of polyol and polyglycol ether groups, for example, as the hydrophilic group. Preferred formulations are those containing nonionic surfactants from at least one of the following groups as o/w emulsifiers: (a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group; (a2) $C_{12/18}$ fatty acid monoesters and diesters of adducts of 1 to 30 moles of ethylene oxide with glycerol; (a3) glycerol monoesters and diesters and sorbitan monoesters and diesters of saturated and unsaturated fatty acids containing 6 to 22 carbon atoms and ethylene oxide adducts thereof; (a4) alkyl monoglycosides and oligoglycosides containing 8 to 22 carbon atoms in the alkyl radical and ethoxylated analogs thereof and (a5) adducts of 15 to 60 moles of ethylene oxide with castor oil and/or hydrogenated castor oil; (a6) polyol esters and, in particular, polyglycerol esters such as, for example, polyglycerol polyricinoleate or polyglycerol poly-12-hydroxystearate. Mixtures of compounds from several of these classes are also suitable. The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051. Zwitterionic surfactants may also be used as emulsifiers. Zwitterionic surfactants are surfactants which contain at least one quaternary ammonium group and at least one carboxylate group and one sulfonate group in the molecule. Particularly suitable zwitterionic surfactants are the so-called betaines, such as the N-alkyl-N,N-dimethylammonium glycinates, for example cocoalkyl dimethylammonium glycinate, N-acylaminopropyl-N,N-dimethylammonium glycinates, for example cocoacyl aminopropyl dimethylammonium glycinate, and 2-alkyl-3-carboxymethyl-3-hydroxyethyl imidazolines containing 8 to 18 carbon atoms in the alkyl or acyl group and cocoacylaminoethylhydroxyethyl carboxymethyl glycinate. The fatty acid amide derivative known under the CTFA name of Cocamidopropyl Betaine is particularly preferred. Other suitable emulsifiers are ampholytic surfactants. Ampholytic surfactants are understood to be surface-active compounds which, in addition to a $C_{8/18}$ alkyl or acyl group, contain at least one free amino group and at least one —COOH or —SO$_3$H group in the molecule, and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkyl aminopropionate, cocoacyl aminoethyl aminopropionate and $C_{12/18}$ acyl sarcosine.

Suitable w/o emulsifiers are: (b1) adducts of 2 to 15 moles of ethylene oxide with castor oil and/or hydrogenated castor oil; (b2) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose); (b3) trialkyl phosphates; (b4) wool wax alcohols; (b5) polysiloxane/polyalkyl polyether copolymers and corresponding derivatives; (b6) mixed esters of pentaerythritol, fatty acids, citric acid and fatty alcohol according to DE-PS 11 65 574 and (b7) polyalkylene glycols.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, LUVIQUAT® (BASF AG, Ludwigshafen, FRG), condensation products of polyglycols and amines, quaternized protein polypeptides such as, for example, Lauryldimonium Hydroxypropyl Hydrolyzed Collagen (LAMEQUAT®L, Gr ünau GmbH), polyethyleneimine, cationic silicone polymers such as, for example, Amidomethicone or Dow Corning, Dow Corning Co., USA, copolymers of adipic acid and dimethylaminohydroxypropyl diethylenetriamine (CARTARETINE®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, JAGUAR®CBS, JAGUAR®C-17, JAGUAR®C-16 of Celanese, USA and quaternized ammonium salt polymers such as, for example, MIRAPOL® A-15, MIRAPOL® AD-1, MIRAPOL® AZ-1 of Miranol, USA.

Suitable silicone compounds are, for example, dimethyl polysiloxanes, methylphenyl polysiloxanes, cyclic silicones and amino-, fatty-acid-, alcohol-, polyether-, epoxy-, fluorine- and/or alkyl-modified silicone compounds. Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetostearyl alcohol. Metal salts of fatty acids, for example magnesium, aluminium and/or zinc stearate, may be used as stabilizers. In the context of the invention, biogenic agents are, for example, plant extracts and vitamin complexes. Suitable preservatives are, for example, phenoxyethanol, formaldehyde solution, parabens, pentanediol or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Farbemittel" of the Farbstoffkommission der Deutschen Forschungsgemeinschaft, published by Verlag Chemie, Weinheim, 1984, pages 81–106.

In all, the auxiliaries and additives may make up 1 to 50 and preferably 5 to 40% by weight of the emulsions.

EXAMPLES

I. Application Examples

Aqueous o/w emulsions were prepared using cetearyl glucoside ($C_{16}$:$C_{18}$=1:1), the corresponding cetearyl alcohol, Caprylic/Capric Triglyceride (MYRITOL® 312, Henkel KGaA) as oil and optionally Hydrogenated Palm Glycerides (MONOMULS® 60-35, Henkel KGaA) as hydrophilic wax. The viscosities of the mixtures were determined by the Brookfield Method in an RVT viscosimeter (20° C., 4 r.p.m., spindle TE, with Helipath). The results are set out in Table 1.

TABLE 1

Viscosities of o/w creams (water ad 100% by weight)

| Ex. | CG % by weight | CA % by weight | HW % by weight | CG:CA | T. Wax % by weight | Oil % by weight | Viscosity Pas |
|---|---|---|---|---|---|---|---|
| 1 | 3.7 | 3.7 | 1.0 | 50:50 | 7.4 | 16 | 500 |
| 2 | 2.7 | 2.7 | 1.0 | 50:50 | 6.4 | 16 | 63 |
| 3 | 2.7 | 2.7 | 2.1 | 50:50 | 7.5 | 16 | 400 |
| C1 | 1.9 | 5.6 | — | 25:75 | 7.5 | 16 | 62 |
| C2 | 3.4 | 9.6 | — | 25:75 | 13.0 | 16 | 460 |

Legend:
CG = Cetearyl oligoglucoside
HW = Hydrophilic wax
CA = Cetearyl alcohol
T. Wax = Total wax (CG + CH + HW)

TABLE 2

II. Formulation Examples
Application Examples (percentages as % by weight; water + preservative ad 100%)

| Formulation | Component | CTFA Name | Content % |
|---|---|---|---|
| O/W multipurpose cream | Cetearyl glucoside | Cetearyl Polyglucose | 1.9 |
| | Cetearyl alcohol | Cetearyl Alcohol | 1.9 |
| | MONOMULS ® 60-35 | Hydrogenated Palm Glycerides | 3.6 |
| | CETIOL ® LC | Coco-Caprylate Caprate | 10.0 |
| | CETIOL ® V | Decyl Oleate | 3.0 |
| | MYRITOL ® 318 | Caprylic/Capric Triglyceride | 1.0 |
| | BAYSILON ® M 350 | | 0.5 |
| | Glycerol | | 3.0 |
| O/W skin cream with vitamin E | Cetearyl glucoside | Cetearyl Polyglucose | 2.6 |
| | Cetearyl alcohol | Cetearyl Alcohol | 2.6 |
| | MONOMULS ® 60-35 | Hydrogenated Palm Glycerides | 1.5 |
| | CETIOL ® J 600 | Oleyl Erucate | 3.0 |
| | CETIOL ® V | Decyl Oleate | 4.0 |
| | CETIOL ® OE | Dicaprylyl Ether | 2.0 |
| | BAYSILON ® M 350 | | 0.5 |
| | MYRITOL ® 318 | Caprylic/Capric Triglyceride | 4.0 |
| | COPHEROL ® F 1300 | Tocopherol | 1.0 |
| | Glycerol | | 3.0 |
| O/W lotion for normal skin | Cetearyl glucoside | Cetearyl Polyglucose | 0.7 |
| | Cetearyl alcohol | Cetearyl Alcohol | 0.7 |
| | MONOMULS ® 60-35 | Hydrogenated Palm Glycerides | 5.0 |
| | CETIOL ® J 600 | Oleyl Erucate | 2.0 |
| | CETIOL ® V | Decyl Oleate | 6.0 |
| | CETIOL ® OE | Dicaprylyl Ether | 2.0 |
| | BAYSILON ® M 350 | | 0.5 |
| | Glycerol | | 3.0 |

TABLE 2-continued

II. Formulation Examples
Application Examples (percentages as % by weight; water + preservative ad 100%)

| Formulation | Component | CTFA Name | Content % |
| --- | --- | --- | --- |
| O/W day cream for sensitive skin | Cetearyl glucoside | Cetearyl polyglucose | 1.2 |
| | Cetearyl alcohol | Cetearyl Alcohol | 1.2 |
| | MONOMULS ® 60-35 | Hydrogenated Palm Glycerides | 4.5 |
| | Almond oil | Almond Oil | 2.0 |
| | CETIOL ® 868 | Octyl Stearate | 6.0 |
| | Isopropyl palmitate | Isopropyl Palmitate | 2.0 |
| | BAYSILON ® M 350 | | 0.5 |
| | Glycerol | | 3.0 |

What is claimed is:

1. An emulsifier consisting essentially of: (a) from about 43% to about 99% by weight of an alkyl and/or an alkenyl oligoglycoside; and (b) from about 1% to about 57% by weight of a fatty alcohol.

2. An emulsifier consisting essentially of: (a) from about 43% to about 90% by weight of an alkyl and/or an alkenyl oligoglycoside; and (b) from about 10% to about 57% by weight of a fatty alcohol.

3. An emulsifier consisting essentially of: (a) from about 45% to about 55% by weight of an alkyl and/or an alkenyl oligoglycoside; and (b) from about 45% to about 55% by weight of a fatty alcohol.

4. The emulsifier of claim 1 wherein said alkyl and/or alkenyl oligoglycoside is a compound of the formula (I):

$$R^1O\text{---}[G]_p \qquad (I)$$

wherein $R^1$ is an alkyl, alkenyl, hydroxysubstituted alkyl, hydroxysubstituted alkenyl radical containing 4 to 54 carbon atoms or a combination thereof, G is a glycoside containing 5 or 6 carbon atoms and p is a number from 1 to 10.

5. The emulsifier of claim 3 wherein $R^1$ is a cetearyl group, an isostearyl group or the residue of a Guerbet alcohol.

6. The emulsifier of claim 1 wherein said fatty alcohol is a compound of the formula (II):

$$R^2OH \qquad (II)$$

wherein $R^2$ is a linear or branched aliphatic or hydroxysubstituted aliphatic hydrocarbon radical containing 6 to 54 carbon atoms and 0 to 3 double bonds.

7. The emulsifier of claim 6 wherein said alcohol is cetearyl alcohol, isostearyl alcohol, Guerbet alcohol, or a combination thereof.

8. An emulsifier consisting essentially of: (a) from about 25% to about 45% by weight of an alkyl and/or an alkenyl oligoglycoside; (b) from about 25% to about 45% by weight of a fatty alcohol; (c) from about 10% to about 50% by weight of a hydrophilic wax.

9. A process for producing an emulsifier comprising the steps of: (1) reacting glucose and an excess of a first fatty alcohol in the presence of an acid catalyst to produce a mixture comprised of an alkyl oligoglucoside and excess fatty alcohol; (2) removing said excess fatty alcohol; and (3) adding an amount of a second fatty alcohol sufficient to form said emulsifier.

10. A process for producing an emulsifier comprising the steps of: (1) reacting glucose and excess fatty alcohol in the presence of an acid catalyst to produce a mixture comprised of an alkyl oligoglucoside and excess fatty alcohol; and (2) adding an amount of said alkyl oligoglucoside sufficient to form said emulsifier.

11. A process for making a o/w emulsion comprising adding to an oil and water mixture an emulsifying-effective amount of an emulsifier of claim 1.

12. An emulsion comprising of the emulsifier of claim 1.

* * * * *